Figure 1:
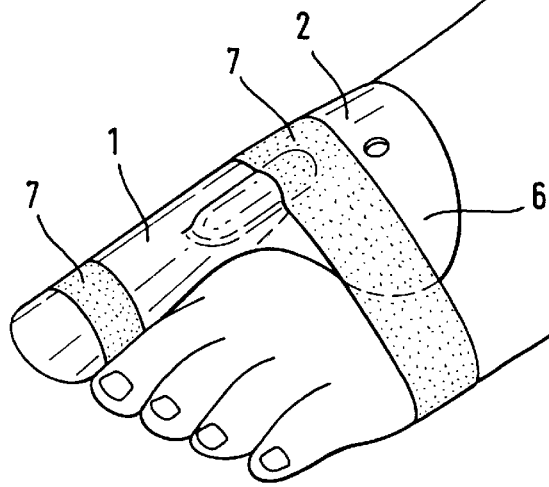

United States Patent
Lockhart

Patent Number: 5,957,875
Date of Patent: Sep. 28, 1999

[54] TOE SPLINT FOR AN OUTER TOE

[75] Inventor: Robert D. Lockhart, Sunnyvale, Calif.

[73] Assignee: Waldemar Link (GmbH & Co.), Germany

[21] Appl. No.: 08/766,943

[22] Filed: Dec. 16, 1996

[30] Foreign Application Priority Data

Sep. 19, 1996 [DE] Germany ........................ 296 16 345 U

[51] Int. Cl.⁶ ............................... A61F 5/00; A61F 13/06
[52] U.S. Cl. ............................................. 602/30; 128/893
[58] Field of Search ................................ 602/5–8, 11, 22, 602/30, 31; 128/880, 889, 892, 893

[56] References Cited

U.S. PATENT DOCUMENTS

| | | | |
|---|---|---|---|
| 1,054,934 | 3/1913 | Packard | 128/893 |
| 2,190,016 | 2/1940 | Day et al. | 602/30 |
| 2,225,896 | 12/1940 | Belknap | 128/880 |
| 2,251,551 | 8/1941 | O'Reilly | 128/880 X |
| 2,357,413 | 9/1944 | McGinnis | 128/880 |
| 2,492,312 | 12/1949 | Muller | 602/30 |
| 2,589,791 | 3/1952 | Fine | 602/30 |
| 3,219,032 | 11/1965 | Levitt | 602/30 |
| 5,154,692 | 10/1992 | Lockhart | 602/30 |

*Primary Examiner*—Richard J. Apley
*Assistant Examiner*—Denise Pothier
*Attorney, Agent, or Firm*—Medlen & Carroll, LLP

[57] ABSTRACT

The invention relates to a toe splint for an outer toe, having a rear holding part, which is to be placed against the metatarsus, and a supporting part, which is integrally connected thereto and is to be placed upon the toe to be supported. The holding part and the supporting part each have a side portion to be placed against the outer edge of the foot or toe. The improvement according to the invention consists in the fact that the side portions are continuously joined in the manner of a splint.

4 Claims, 2 Drawing Sheets

U.S. Patent       Sep. 28, 1999       Sheet 1 of 2       5,957,875

TOE SPLINT FOR AN OUTER TOE

The invention relates to a toe splint for an outer toe. By this is meant the big toe or little toe. The toe splint comprises a rear holding part, which is to be placed against the metatarsus, and a supporting part, which is integrally connected thereto and is to be placed upon the toe to be supported. The holding part and the supporting part have apart from the upper portion, which is to be placed in each case upon the metatarsus or toe, a side portion, which placed against the outer edge of the foot or toe.

A toe splint of the type described is known from U.S. Pat. No. 5,154,692. This requires that between the holding part and the supporting part there is provided a third part, which connects the holding part and the supporting part and which is laterally retracted in order to prevent contact in this region between the toe splint and that part of the toe which is present at this location. This not only gives rise to stability problems, but can also result in harmful friction between the front edge of the rear side portion and the rear edge of the front side portion and the outer edge of the foot or toe.

The invention avoids these drawbacks by virtue of the fact that the side portions are continuously joined in the manner of a splint.

The side portion, which runs continuously from back to front and is angled-off relative to the upper portion to be placed upon the upper side of the metatarsus or toe, lends high stability to the splint and therefore allows it to be made from a thinner, more ductile material. This, in turn, makes the splint—apart from its longitudinal rigidity—more ductile, thereby enabling it to adapt better to the shape of the foot or to any momentary stress. Despite offering adequate support, it is therefore much more comfortable to wear than the known toe splint.

In its embodiment as a big-toe splint, it expediently has in the transition region from the holding part to the supporting part a longitudinal rib which is concave on the lower side and projects upwards and which additionally stiffens the connecting region between holding part a nd supporting part and further has the advantage that the extensor tendon of the big toe remains free in the region of the toe root.

If in its embodiment as a little-toe splint, in the transition region from the holding part to the supporting part a recessed connecting face is expediently provided between the inner margin of the supporting part and the diagonally forward, inward running front margin of the holding part. This also results in longitudinal stiffening and allows the supporting part to be raised in the region of the toe root.

Figure 2:
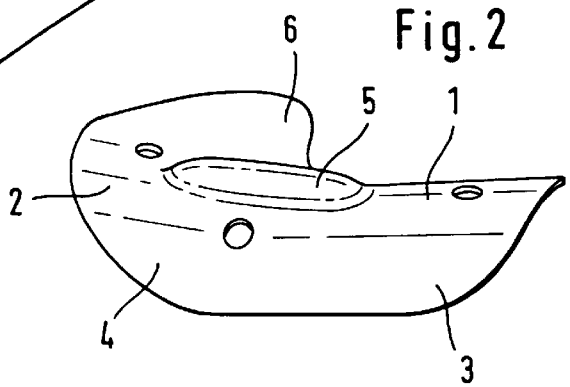
Figure 3:
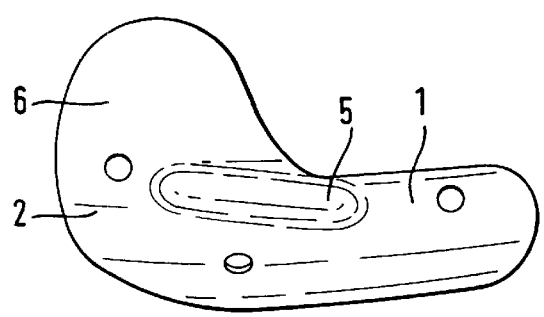
Figure 4:
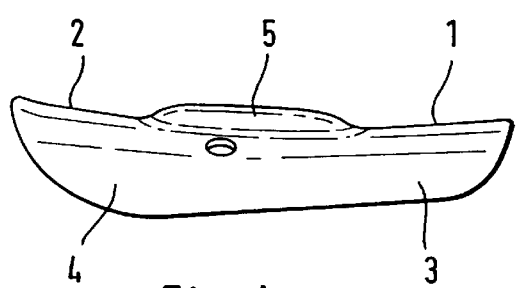
Figure 5:
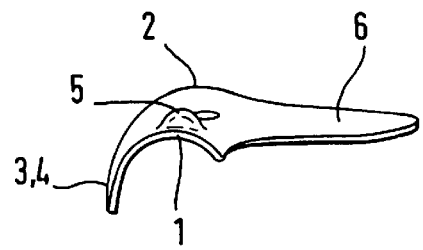
Figure 6:
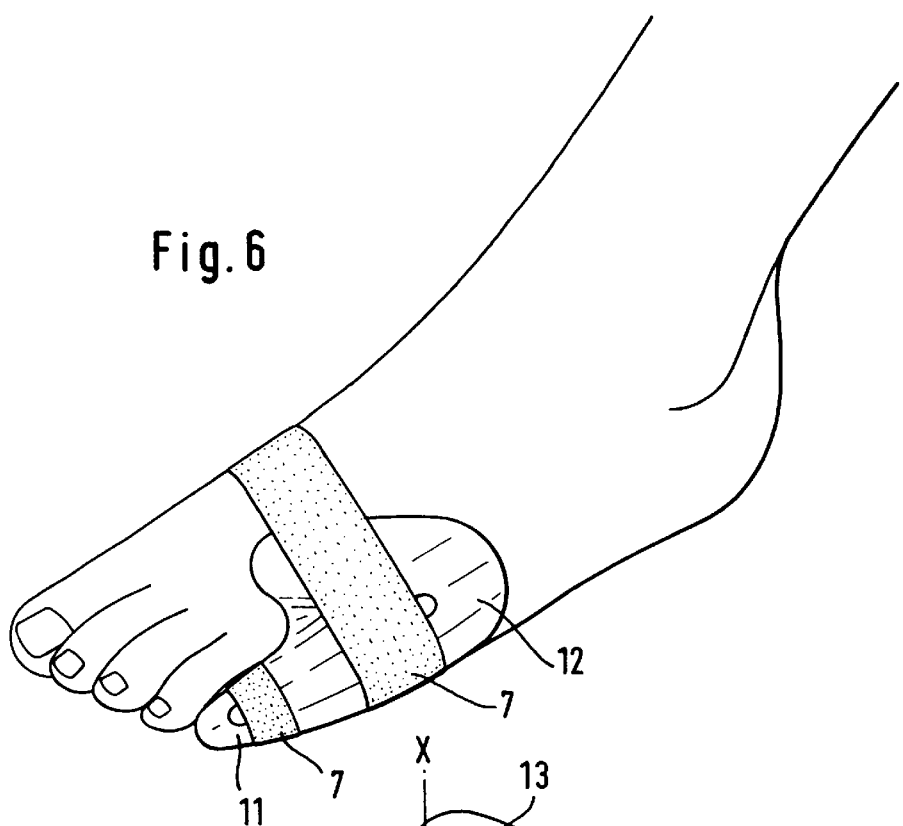
Figure 7:
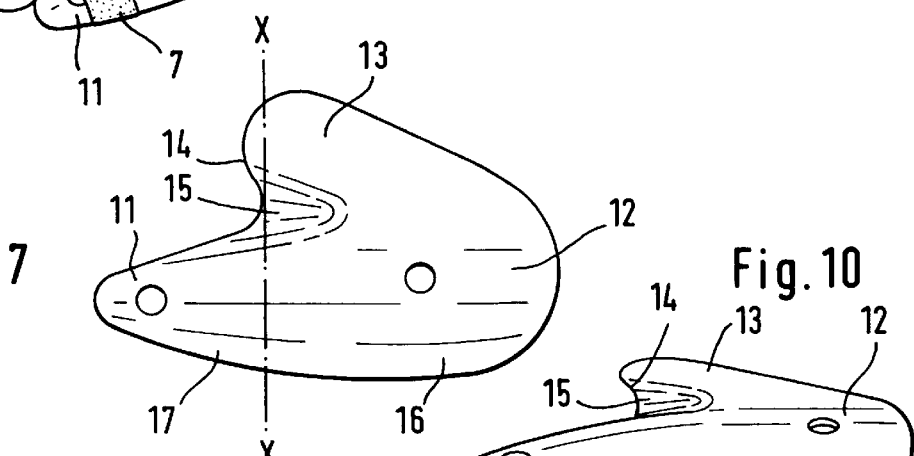
Figure 10:
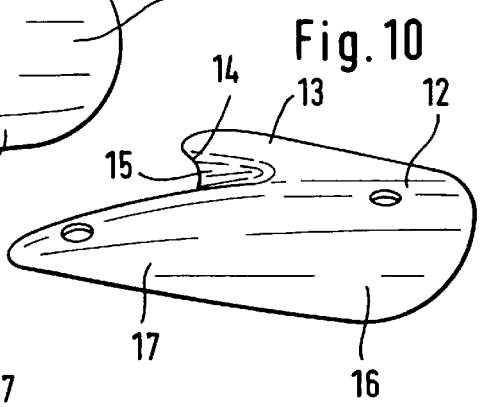
Figure 8:
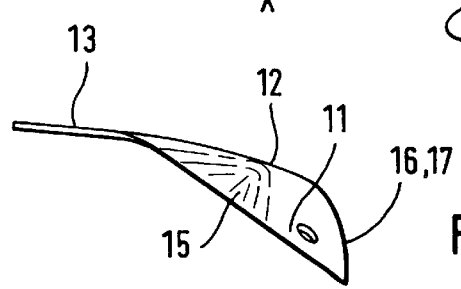
Figure 9:
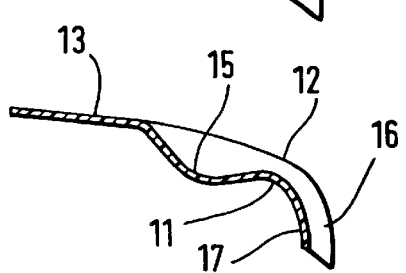

The invention is explained in greater detail below with reference to the drawing depicting advantageous illustrative embodiments, in which:

FIG. 1 show s the perspective representation of a left foot with applied big-toe splint, FIG. 2 shows a view of the big-toe splint from diagonally above, side-on, at the front, FIG. 3 shows a top view, FIG. 4 shows a side view, FIG. 5 shows a front view, FIG. 6 shows the representation of a left foot with applied little-toe splint, FIG. 7 shows a top view of the little-toe splint, FIG. 8 shows a front view, FIG. 9 shows a section along the line X—X of FIG. 7, and FIG. 10 shows a side view.

The splints shown consist of a moulded flat plastics material of 1.5 mm thickness, for example, and having a flexibility as exhibited, for example, by firm cardboard of this thickness. The material in question is expediently a thermoplastic material which can be remoulded at comfortably manageable temperatures (particularly 50 to 80° C., preferably 60 to 70° C.). Different splints are provided for the right and left foot.

The big-toe splint according to FIGS. 1 to 5 comprises a relatively narrow, slenderly protruding supporting-part 1, the width and length of which roughly correspond to that of the big toe, and a holding part 2, which is attached to the rear of the said supporting part and is enlarged on the foot side to double to triple the width and has a length which is not substantially less than that of the supporting part 1.

In accordance with the shape of the big toe, the supporting part 1 is uniformly curved in cross-section over virtually its entire length, as can be seen in FIG. 5. On the outer side it is lengthened to create a side portion 3 which is virtually vertical during use and which merges in the rearward direction, remaining roughly the same in cross-section, into the side portion 4 of the holding part 2. The side portion 3, 4 runs roughly straight throughout its length. Slight curvatures can be provided, for example, to take into account the metatarsophalangeal joint of the big toe.

The continuous side portion 3, 4 connected to the back 1, 2 of the splint, which splint back is angled-off in relation to the said side portion, lends considerable rigidity to the splint. The continuous shape of the side portion 3, 4 also avoids the formation of any edges in the transition region from the supporting part 1 to the holding part 2, which edges could rub against the edge of the foot or against the toe.

Whilst the supporting part is curved in cross-section to match the shape of the toe, the holding part runs on the foot side in a roughly flat plane 6. In side view, it rises somewhat towards the rear in comparison with the course of the supporting part 1.

In the transition region from the supporting part 1 to the holding part 2, i.e. roughly in the region of the metatarsophalangeal joint of the big toe, a rib 5 rises up from the upper side of the splint, the width of which rib is of the order of magnitude of 1 cm and the length of which rib is around 3 to 6 cm, preferably about 4 cm. It is arched slightly upwards and is hollow on the lower side, thereby offering space to the extensor tendon of the big toe. It also stiffens the splint in the transition region from the supporting part 1 to the holding part 2, which region is particularly subjected to bending stress.

Whilst maintaining this basic shape, several size categories for this splint can be provided for practical use. It is expediently padded on the lower side with a layer of felt or the like.

For use, it is fastened on the one hand by the holding part 2 to the metatarsus and on the other hand by the supporting part 1 to the big toe by means of adhesive tape 7.

A fundamental advantage of the splint according to the invention consists in the fact that the simple basic shape on the one hand is optimally matched to the shape of the foot and on the other hand can be used even in cases of individually deformed feet.

The little-toe splint according to FIGS. 6 to 10 likewise comprises a supporting part 11, which is assigned to the toe to be supported, and a holding part 12, the upper side of which runs through essentially flatly in the longitudinal direction and arched slightly upwards. The holding part 12 widens on the foot side in the form of the contact face 13. Its front boundary 14 runs diagonally forwards—in accordance with the front limit of the metatarsus. In the transition region from the face 13 to the supporting part 1 and to the front end of the holding part 12, a recess 15 is cut, which produces a considerable stiffening of the splint in this region.

The side portions 16, 17 of the holding part and supporting part merge flatly together. They can be curved slightly outwards to provide more space, where necessary, for the metatarsophalangeal and interphalangeal joints. Combined with the top faces of the parts 11 and 12, which faces are angled-off relative to the side portion, they lend considerable rigidity to the splint, whilst at the same time the splint material is conveniently flexible. For the support of the toes, the side portion is at least as important as the top part, since, at least in the region of the little toe, it is just as elongated or is even indeed wider than the top part.

As previously explained with respect to the big-toe splint, the little-toe splint is similarly held by two adhesive tapes 7, which on the one hand secure the holding part 12 to the metatarsus and on the other hand secure the supporting part 11 to the little toe.

I claim:

1. A method for supporting a toe, comprising:
   a) providing:
      i) a toe splint for an outer toe, comprising: i) a rear holding part configured to be positioned against the metatarsus; and ii) a front supporting part configured to be placed on the outer toe so as to cover the toe, said front supporting part integrally connected to said rear holding part with a transition region between said rear holding part and said front supporting part so as to provide longitudinal rigidity, said rear holding part and said front supporting part each having a side portion continuously joined together; and
      ii) a patient having an injured outer toe;
   b) positioning said rear holding part of said toe splint against the dorsal metatarsus of said patient and placing said front part of said toe splint onto the top of said injured outer toe so as to cover said injured outer toe, said positioning of said splint leaving the extensor tendon free in the region of the toe root.

2. The method of claim 1, wherein said injured toe is the outer big toe.

3. The method of claim 1, wherein said transition region comprises a longitudinal rib.

4. The method of claim 3, wherein said longitudinal rib is concave on the under side and projects upward, said concave rib providing a space for said extensor tendon.

* * * * *